United States Patent [19]

Ashiku

[11] Patent Number: 4,861,266
[45] Date of Patent: Aug. 29, 1989

[54] DENTAL ASPIRATOR VALVE AND VALVE SHEATH

[76] Inventor: Mark Ashiku, 475 Eastlick, Apt. 1, Ukiah, Calif. 95482

[21] Appl. No.: 171,561

[22] Filed: Mar. 22, 1988

[51] Int. Cl.⁴ .............................................. A61C 17/04
[52] U.S. Cl. ...................................................... 433/95
[58] Field of Search ....................... 433/95, 92, 100, 96

[56] References Cited

U.S. PATENT DOCUMENTS

| | | | |
|---|---|---|---|
| 961,901 | 6/1910 | Seagrave | 137/596 |
| 1,437,940 | 12/1922 | Heath | 423/499 |
| 2,711,586 | 6/1955 | Groves | 433/95 |
| 3,299,511 | 1/1967 | Hutson | 433/96 |
| 3,476,144 | 11/1969 | Krantz | 433/92 |
| 4,081,176 | 3/1978 | Johnson | 251/342 |
| 4,083,383 | 4/1978 | Antoniello | 137/616.7 |
| 4,200,123 | 4/1980 | Brandelli | 137/625.4 |
| 4,397,640 | 8/1983 | Haug et al. | 433/95 |
| 4,586,900 | 5/1986 | Hymanson et al. | 433/96 |

*Primary Examiner*—Robert Peshock
*Attorney, Agent, or Firm*—Flehr, Hohbach, Test, Albritton & Herbert

[57] ABSTRACT

A dental aspirator valve and sheath assembly is provided comprising an aspirator valve piece which is semi-permanently attached to the vacuum system and a removable sheath which is sterilizable and fits over the vacuum piece. The valve in the aspirator valve piece is indirectly operable through a handle on the sheath which mechanically engages the valve when the sheath is in place.

2 Claims, 2 Drawing Sheets

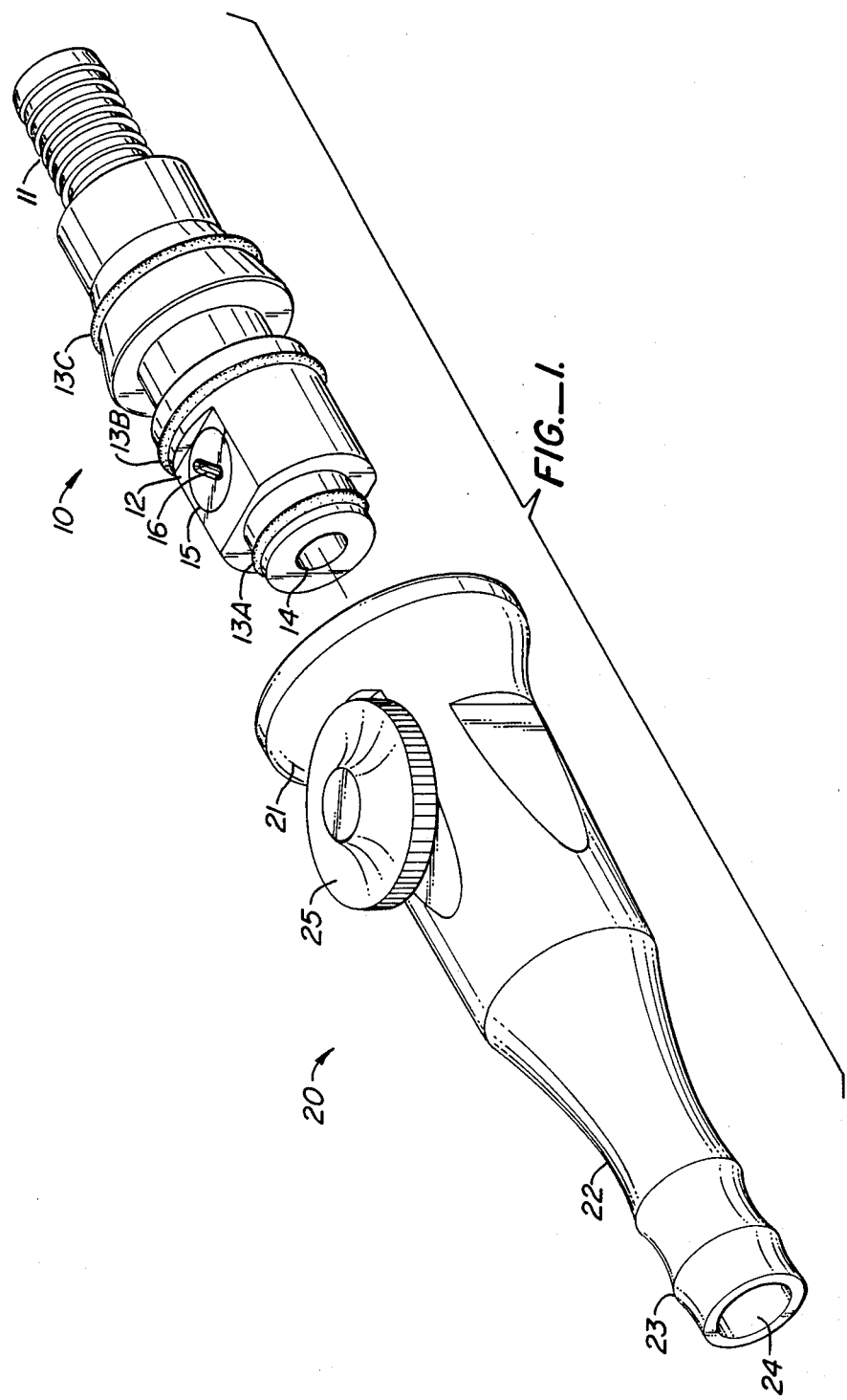
FIG._1.

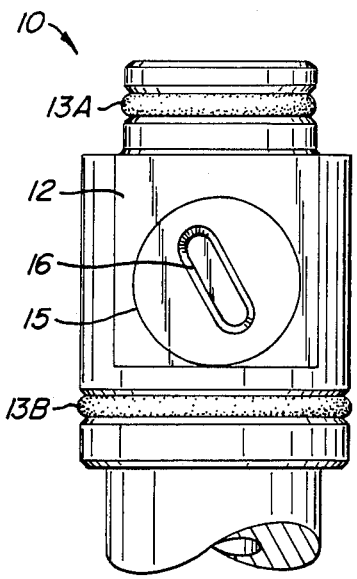
FIG._2A.
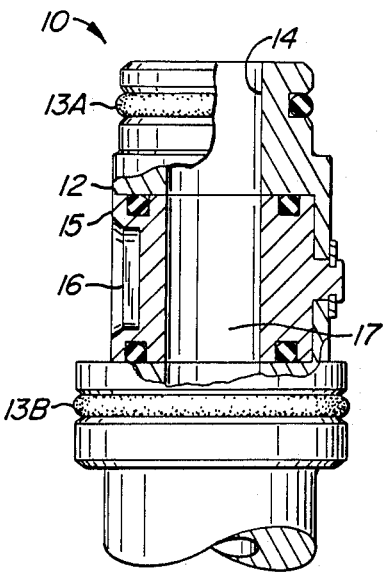
FIG._2B.
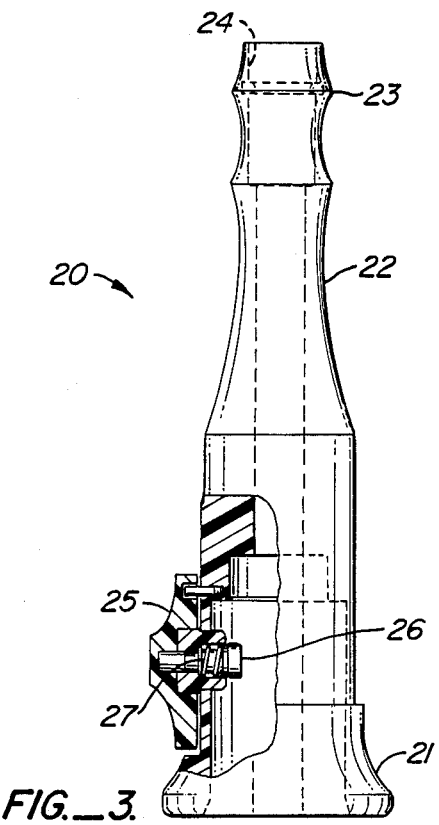
FIG._3.

DENTAL ASPIRATOR VALVE AND VALVE SHEATH

The present invention is directed to a dental aspirator valve and sheath therefor wherein the sheath, used to remove liquid and debris from a patient's mouth, is sterilizable, and the dental aspirator valve is removably attachable to the sheath semi-permanently attached to the vacuum system, while being indirectly operable from a sterilized handle on the sheath.

BACKGROUND OF THE INVENTION

It is desirable for convenience and for rapid and effective sterilization procedures within a dental office to have a hand-held aspirator piece for ejection, siphoning and aspiration connected to a high-flow or low-flow air vacuum system, which also accommodates a valve at or near the hand-held portion of the aspirator tip so that the dentist need not unduly readjust his hand or body position in order to apply and stop the suction. This need for close juxtaposition of the valve and the hand-held portion of the aspirator tip creates a problem in that the hand-held piece which comes in contact with the patient's mouth needs to be removable to be sterilized. Heretofore the solution to this problem has led to the development of detachable aspirators which attempt to solve the problem in one of two ways. One apparent approach is to design a sterilizable aspirator tip which is removable from the rest of the aspirator and valve assembly. This, however, means that either the valve must be located distant from the aspirator tip, so that in most instances the operator must readjust his hand and body position while working to reach the valve or, alternatively, if the valve is located near the sterilized aspirator tip, the operator must touch the nonsterilized portion while he or she is working on the patient's mouth, in order to turn the vacuum system on and off, thus leading to nonsterile techniques. Another way of approaching this problem has been to design an aspirator tip integrated with the valve assembly and vacuum hose. This means that there must be another method of turning off the aspirator system distant from the removable valve and that the vacuum tubing must be sterilized along with the aspirator and valve, thus leading to an unwieldy device which must be carried to and from the sterilizer between uses on different patients.

To solve the above problems in an advantageous and improved way, according to the present invention there is provided a dental aspirator valve and valve sheath assembly comprising two components which allows for manipulation of the valve without direct contact of nonsterile areas. The invention further provides a system whereby a vacuum system may be maintained, i.e., whereby the valve remains attached to the vacuum hose, while the sterilizable portions of the aspirator can be removed for sterilization without breaking the vacuum. This eliminates the need for a second valve to close and maintain the vacuum system.

Furthermore, due to advantageous design of a sheath according to the present invention, the operator's hand is restricted to the sheath and kept from sliding to and contacting the nonsterile valve and hose. Furthermore, because a valve according to the present invention remains attached to the vacuum system and vacuum hose and is not removed to be sterilized, the valve itself requires less maintenance and will be less of a hazard to personnel involved during sterilization. Further advantages of the invention will be apparent from the following description of the preferred embodiments of the invention and from the appended drawings.

SUMMARY OF THE INVENTION

The present invention provides a dental aspirator valve and sheath assembly comprising an aspirator valve piece comprising an elongated housing adapted at a first end for attachment to a vacuum source and adapted at the second end for vacuum-tight attachment to a sheath. The valve piece also has a valve control which can be remotely controlled through a corresponding control handle on the sheath. The assembly also comprises a sheath comprising an open-ended hollow housing and a control handle which is adapted to remotely operate the valve control of the aspirator valve piece upon placement of the sheath over the second end of the valve piece.

BRIEF DESCRIPTION OF THE DRAWINGS

In the accompanying drawings FIG. 1 is an exploded perspective view of the preferred embodiments of a dental aspirator valve and sheath assembly according to the present invention;

FIG. 2 shows front (FIG. 2A) and partial cross-section (FIG. 2B) elevations of the aspirator valve piece shown in FIG. 1;

FIG. 3 is a partial cross-section elevation of the valve sheath shown in FIG. 1.

DESCRIPTION OF THE PREFERRED EMBODIMENTS

According to the present invention there is provided a two-piece assembly. One of the pieces is a dental aspirator valve comprising an elongated housing adapted at one end for attachment to a vacuum source. It will be appreciated that the end which is adapted for attachment, semi-permanently or removably, to the vacuum source can be designed to be used with different vacuum equipment by an appropriate connection thereto. The other end of the aspirator valve piece is adapted to be tightly fitting with a sheath, described hereinbelow. A vacuum-type seal will be formed upon engagement of the aspirator valve piece with the sheath by use, for example, of annular sealing rings on the aspirator valve piece which form tight seals with the inner diameter of the sheath when the sheath is fitted over the aspirator valve piece. The aspirator valve piece will also accommodate a valve for opening and closing access to the vacuum. The valve will be operable by the operator, not by directly touching the valve piece, but indirectly through an engagement device, such as a slotted barrel, so that the slot is engagable by a corresponding flat-ended projection on the sheath. When the sheath is fitted onto the aspirator valve piece, an exterior handle on the sheath, attached to a flat-ended projection in the interior of the sheath, engages the slot on the end of the barrel which opens and closes the valve, thus providing for operation of the valve by the operator without direct contact with the aspirator valve piece. The secure engagement of the flat-ended projection with the slot also locks the sheath onto the valve piece.

The aspirator valve piece may be removed for sterilization as part of sanitary practice within an office, however, it is not intended to be sterilized for each different patient, and thus is a semi-permanent piece for use with the vacuum system. In this regard, the aspirator valve piece may be made out of a sturdy material, such as stainless steel.

The sheath which fits over the aspirator valve piece is adapted at one end to receive the aspirator valve piece and at the other end to receive various tips for insertion into the patient's mouth, or it may be used without such tips. The end to receive the valve piece is fluted, which also allows the operator's hand to be restricted to the sheath to prevent sliding into or contacting the aspirator valve piece. The exterior of the sheath accommodates a handle which will be directly operated by the operator. The handle will be suitably operable by rotation, sliding, or other movement, depending in part upon the design of the valve in the valve piece and upon the way in which the valve is engaged to the handle on the sheath. In a preferred device, the handle is attached to an axle which, on the interior of the sheath, has a mechanical means for engagement, such as a flat projection, specifically designed to engage a slotted end on a rotatably operable aspirator valve on the aspirator valve piece. The axle for the handle on the sheath may be adapted with a spring so that the mechanical engagement between the slot and the flat projection is secure while the sheath is in place, thus also preventing separation of the sheath from the valve piece. The sheath will be sterilized and may be, for example, made of any type of sterilizable plastic material which can withstand the temperatures of steam sterilizing equipment used in a dental office. It is contemplated that the operator will have a plurality of sheaths so that he or she may interchange them as needed whenever a new sterile sheath is required to work on a different patient.

It will be appreciated that various types of valves may be utilized in the valve piece which may be rotatably operable, such as a drilled barrel or butterfly; slide-operated or operated by other types of movement. Furthermore, the means of engagement of the valve (on the valve piece) with the handle (on the sheath) may be, for example, by male and female hex-head, or even by a powerful magnet.

The valve may also be made to be operable by forming the valve piece as two portions joined at a pivoting or otherwise articulating junction. By providing the valve at the junction, the valve may be operated by articulating, or pivoting, the two portions of the valve piece.

The invention will now be described further by way of reference to the accompanying drawings which represent preferred embodiments of the invention. The invention, however, is not intended to be limited to the precise design of the embodiments described below in that various modifications and alterations will be readily apparent which are within the scope and spirit of the present invention from a reading of the description herein and from practice of the invention.

Referring to FIG. 1, there is shown an exploded perspective view of a preferred embodiment of the dental aspirator valve and valve sheath assembly according to the present invention. The aspirator valve piece 10 accommodates a longitudinal orifice 14 for passage of air, fluids and particulate matter therethrough. At one end of the aspirator valve piece 10 there is a grooved adapter 11 for receiving a flexible tube (not shown) attached to the vacuum source (not shown). Located toward the other end of the valve piece 10 is a valve (not shown) and the exterior rotatably operable mechanical engagement piece 15 for the valve accommodating a slot 16. The piece 15 does not extend beyond the bevelled surface 12 so as not to interfere with the placement of the sheath 20 when it is placed over the aspirator valve piece 10. There is shown annular rubber gaskets 13A and 13B which form a tight seal when the sheath 20 is placed thereover. The sheath 20 also accommodates a longitudinal passageway 24 for passage of air and fluids therethrough. One end 21 of the sheath 20 is fluted so that the operator's hand will be prevented from slipping onto the aspirator piece 10. The other end 22 is narrow and may have annular projections 23 for accommodating auxiliary tips for use in a patient's mouth. The exterior handle 25 is to be directly operable by the operator to manipulate the engagement piece 15 through slot 16.

Still referring to FIG. 1, annular gasket 13C is provided to provide friction against rotational slippage of piece 10 when engaging or disengaging sheath 20 to piece 10. Gasket 13C will be in contact with a suitable receptacle (not shown) which holds piece 10 when not in use. Mounting sheath 20 onto piece 10 while the latter is still in place in its receptacle might otherwise cause rotation of piece 10 while the operator is selecting proper alignment for engagement. This rotation is prevented by the frictional contact between gasket 13C and the receptacle. Any receptacle will be suitable as long as sufficient force is applied upon gasket 13C by the receptacle. It will be appreciated that other means of restraining rotational movement of piece 10 in a receptacle may be used in place of or in conjunction with gasket 13C, such as gears, magnets, etc.

Referring to FIG. 2 there are shown two side elevations, A and B, of the aspirator valve piece 10. The annular rubber sealing rings 13A and 13B, the bevelled surface 12, the rotatably operable piece 15 with slot 16 and the interior longitudinal passageway 14 described in connection with FIG. 1 are shown in further detail. Additional detail shown in FIG. 2B is the valve 17 which is operable to open or close the passageway 14.

Referring to FIG. 3 there is shown a partial cross-sectional elevation of the sheath 20 of FIG. 1. The fluted end 21 and the elongated end 22, annular projections 23, longitudinal interior passageway 24 and exterior handle 25 are shown as described in connection with FIG. 1, in partial cutaway section. The flattened end 26 is located in a position so as to be mechanically engageable with slot 16 on the aspirator valve piece 10 when the sheath 20 and the valve piece 10 are securely fitted together. The central axle to which the handle 25 is attached is movable to a limited extent and tension is held by spring 27 to exert a constant inward force on the flattened end 26 so that when the flattened end 26 so that when end 26 and slot 16 are engaged, the engagement will remain secure, and prevent disengagement of sheath 20 from piece 10.

In use, the aspirator valve piece 10 is connected to a vacuum unit, such as via flexible plastic tubing, which securely fits onto grooved end 11. Then, after sterilization, the sheath 20 is placed over the free end of the aspirator valve piece 10, tightly engaged with gaskets 13A and 13B to form an airtight fit. Upon fitting sheath 20 over aspirator piece 10, the end 26 is brought into engagement with slot 16. The operator, during use, will hold the sheath 20 with the fluted end 21 preventing his or her hand from slipping onto the nonsterilized aspirator valve piece 10. Operation of the valve to open and close the vacuum system is done by rotating handle 25 on the sheath 20.

It is understood that the invention is not intended to be restricted by the description of the preferred embodiments above and that the invention shall only be limited by the scope of the following claims.

I claim:

1. A dental aspirator valve and sheath assembly comprising an aspirator valve piece comprising an elongated housing adapted at a first end for attachment to a vacuum source and adapted at the second end to securely receive a sheath thereover, said piece also accommodating valve means operable by mechanical engagement means; and a sheath comprising an open-ended hollow housing and handle wherein said handle is adapted to mechanically engage said mechanical engagement means on said aspirator valve piece upon securing said sheath over said second end of said aspirator valve piece.

2. An assembly according to claim 1 wherein said mechanical engagement means comprises a slot located on said valve means and said handle is rotatably operable and is located on the exterior of said sheath and attached to an axle, one end of which is flattened and extends into the interior of said housing to be engagable with said slot.

* * * * *